US008924036B2

(12) United States Patent
McKinnon

(10) Patent No.: US 8,924,036 B2
(45) Date of Patent: Dec. 30, 2014

(54) SYSTEM AND METHOD FOR HEATING AND INSULATING CONTRAST MEDIA

(75) Inventor: Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 504 days.

(21) Appl. No.: 12/797,819

(22) Filed: Jun. 10, 2010

(65) Prior Publication Data
US 2011/0307117 A1    Dec. 15, 2011

(51) Int. Cl.
*G05D 23/00*  (2006.01)
*A61M 5/44*  (2006.01)
*A61F 7/00*  (2006.01)
*A61B 6/00*  (2006.01)
*A61B 19/00*  (2006.01)

(52) U.S. Cl.
CPC ............... *A61F 7/0085* (2013.01); *A61M 5/44* (2013.01); *A61B 6/504* (2013.01); *A61F 2007/0071* (2013.01); *A61B 2019/448* (2013.01); *A61F 2007/0095* (2013.01)
USPC ............... 700/300; 700/299; 219/386

(58) Field of Classification Search
USPC .................. 700/299–300; 600/300; 392/470; 219/386
See application file for complete search history.

(56) References Cited

U.S. PATENT DOCUMENTS

| 2004/0170409 A1* | 9/2004 | Faries, Jr. et al. ............. 392/470 |
| 2007/0015975 A1* | 1/2007 | Faries et al. .................. 600/300 |
| 2008/0306443 A1 | 12/2008 | Neer et al. |
| 2012/0053457 A1* | 3/2012 | Fago ............................ 600/432 |

FOREIGN PATENT DOCUMENTS

| CH | 648486 A5 | 3/1985 |
| EP | 1 987 852 A2 | 11/2008 |
| WO | WO 03/030790 A1 | 4/2003 |
| WO | WO 2009/064718 A1 | 5/2009 |

\* cited by examiner

*Primary Examiner* — Mohammad Ali
*Assistant Examiner* — Nathan Laughlin
(74) *Attorney, Agent, or Firm* — Jeanne Lukasavage; Craig Metcalf; Kirton McConkie

(57) ABSTRACT

A system for heating and insulating contrast media is disclosed herein. A thermal insulating cover sized to cover at least a portion of a contrast media container is provided with a heating element. A temperature sensor measures the temperature of the contrast media and communicates this temperature to a temperature controller, which controls the heating element in order to maintain the contrast media near a predetermined temperature. Temperature data is transmitted to a computer system by a data communicator.

14 Claims, 4 Drawing Sheets

SYSTEM AND METHOD FOR HEATING AND INSULATING CONTRAST MEDIA

BACKGROUND OF THE INVENTION

The present disclosure relates to contrast media used in imaging procedures, such as magnetic resonance (MR), computed tomography (CT) imaging, and X-ray imaging. Contrast media is a radiopaque substance used in radiography to enhance the contrast of structures or fluids within the body to permit medical imaging. When contrast media is introduced into a patient, for example, into a patient's vasculature, it clarifies the anatomy to imaging devices and enables more detailed radiographic images. During imaging, contrast media enables body structures through which the contrast media flows, particularly blood vessels and the gastrointestinal tract, to be visibly distinguished in the resulting image. Common intravascular contrast media fluids include iodine based, or gadolinium based solutions.

Some diagnostic imaging procedures required the infusion of large quantities of contrast media into a patient infused at very high speeds. For example, some diagnostic imaging procedures utilize contrast media to improve lesion conspicuity in an effort to increase early diagnostic yield. Such a procedure necessitates viscous contrast media to be injected by a specialized "power injector" pump intravenously at very high flow rates, which establishes a contrast bolus or small plug of contrast media in the blood stream of the patient which results in enhanced image quality. The speed of these infusions combined with the viscosity of the contrast media fluids can cause damage to the patient's vasculature.

To establish a contrast bolus or small plug of contrast media in the bloodstream of the patient, the viscous contrast media is injected by a specialized "power injector" pump intravenously at very high flow rates. Power injection procedures generate high pressures within the infusion system, thereby requiring specialized vascular access devices, extension sets, media transfer set, pump syringes, and bulk or pre-filled contrast media syringes. As the concentration (and thereby viscosity) and infusion rate of the contrast media are increased, bolus density also increases resulting in better image quality via computed tomography (CT) attenuation. Therefore, a current trend in healthcare is to increase the bolus density of the contrast media by increasing both the concentration of the contrast media and the rate at which the media is infused into the patient, all of which ultimately drives system pressure requirements higher.

Intravenous infusion rates may be defined as either routine, generally up to 999 cubic centimeters per hour (cc/hr), or rapid, generally between about 999 cc/hr and 90,000 cc/hr (1.5 liters per minute) or higher. For some diagnostic procedures utilizing viscous contrast media, an injection rate of about 1 to 10 ml/second is needed to ensure sufficient bolus concentration. Power injections of viscous media at this injection rate produce significant complications as a result of the high pressures involved. The complications are caused by the combination of the high speed injections and the high fluid viscosity causes of contrast media.

While it is known that contrast media should preferably be heated prior to administration, clinical observations reveal that medical personnel generally do not administer heated contrast media during imaging procedures. This phenomenon is generally caused by medical personnel's failure to preheat the contrast media or a failure to maintain the contrast media at a preheated temperature before and during use. Preheating the contrast media allows for a more comfortable infusion to the patient, as well as a reduction in fluid viscosity, which may decrease the occurrence of complications. Studies have found that the viscosity of some contrast media is reduced by approximately 50% when the media is preheated from 22 degrees Celsius to 35 degrees Celsius. This dramatic decrease in viscosity can produce significantly fewer procedural complications during high speed injections.

Clinical observations have also revealed that the specific reasons for not administering heated contrast media are generally two-fold. First, regulations from medical accreditation bodies, such as the Joint Commission Accreditation body (JCAHO), strictly regulate medicaments that are heated, requiring detailed logs, records, and container tracking. Additionally, under some the regulations, some unused medicaments must be discarded after a certain lapse of time, such as twenty-four hours after being heated. These regulations are sufficiently burdensome that some medical personnel forego heating the contrast media in order to avoid the JACHO requirements. Thus, the understood benefits of preheating contrast media are not realized because it is practically too difficult to repeatedly measure and record the contrast media temperature; track the specific contrast media containers; and continually reheat the contrast media once it has begun to cool down.

The second reason for failure to administer heated contrast media is the natural delays involved in imaging during which time heated contrast media is allowed to cool. Imaging procedures required setting up the imaging device, which generally includes coupling the contrast media to the imaging device, and then conducting several imaging sessions. Generally, the contrast media is only heated prior to the first imaging session, during which time it cools before it is used for subsequent imaging sessions. For example, it is common for contrast media to be contained in 0.5 liter containers. These large containers provide contrast for multiple imaging sessions, such as three to five discrete sessions. However, prior to or during of the first imaging session, the contrast media cools to room temperature. Accordingly, subsequent imaging patients receive doses of room temperature infusions of contrast media which has a much higher viscosity and tends to be less comfortable to the patient.

Accordingly, there is a long-felt need in the art for solutions to the problem of contrast media heating and temperature maintenance. Such solutions are disclosed herein.

BRIEF SUMMARY OF THE INVENTION

The present invention has been developed in response to problems and needs in the art that have not yet been fully resolved by currently available systems, devices, and methods. Thus, these developed systems, devices, and methods heat and insulate contrast media fluid while automatically or semi-automatically recording the temperature of the fluid. In some implementations, a preheated container of contrast media is covered, at least in part, in an insulating cover to insulate the container prior to and during the use of the fluid. The insulating cover may include a heating element and temperature controller, such as a thermostat, to reheat the contrast fluid before, during, and after use.

The system also includes components which identify and record both the temperature of the contrast media fluid and identification data for the container, such as a container number. This information is automatically or semi-automatically acquired by an identification reader. Thereafter this information is transferred to an external computer system where the information can be processed and inserted into a record. Thus, the practical difficulties of measuring and recording temperature data are overcome by the present embodiments of the systems and methods herein described. Finally, the insulating cover ensures that properly heated media contrast fluid is delivered to a patient regardless of when the fluid was initially preheated.

In one aspect, a system for heating and insulating contrast media includes a thermal insulating cover sized to cover at least a portion of a contrast media container. A heating element is coupled to the thermal insulating cover. A temperature sensor is in contact with the container of contrast media or the contrast media fluid. A temperature controller is in electronic communication with the heating element and the temperature sensor. The temperature controller has logical controls that receive contrast media temperature data from the temperature sensor and control the function of the heating element. A data communicator is configured to transmit temperature data to an external computer system, the data communicator is coupled to the thermal insulating cover.

Implementations may include one or more of the following features. The system may also include a preheating device. The preheating device may have a second data communicator to transmit contrast media temperature data to an external, electronic database. The contrast media container may include an identification element, and the system may include an identification reader in the vicinity of the thermal insulating cover that reads the identification element. The data communicator may be electronically coupled to the identification reader to receive identification data from the identification reader. Temperature data may include periodic temperature measurements of the contrast media fluid temperature.

In another aspect, a contrast media insulating and heating device includes a thermal insulating cover sized to cover at least a portion of a contrast media container. A heating element is coupled to the thermal insulating cover. A temperature sensor is in contact with the container of contrast media or the contrast media fluid. A temperature controller is in electronic communication with the heating element and the temperature sensor. The temperature controller has logical controls that receive contrast media temperature data from the temperature sensor and controls the function of the heating element.

Implementations may include, a container may include an identification element and an identification reader coupled to the thermal insulating cover. The device may include a data communicator. The temperature sensor may be disposed on a fluid spike. The heating element may be an active heating element. Alternatively, the heating element may be an ohmic heating element.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
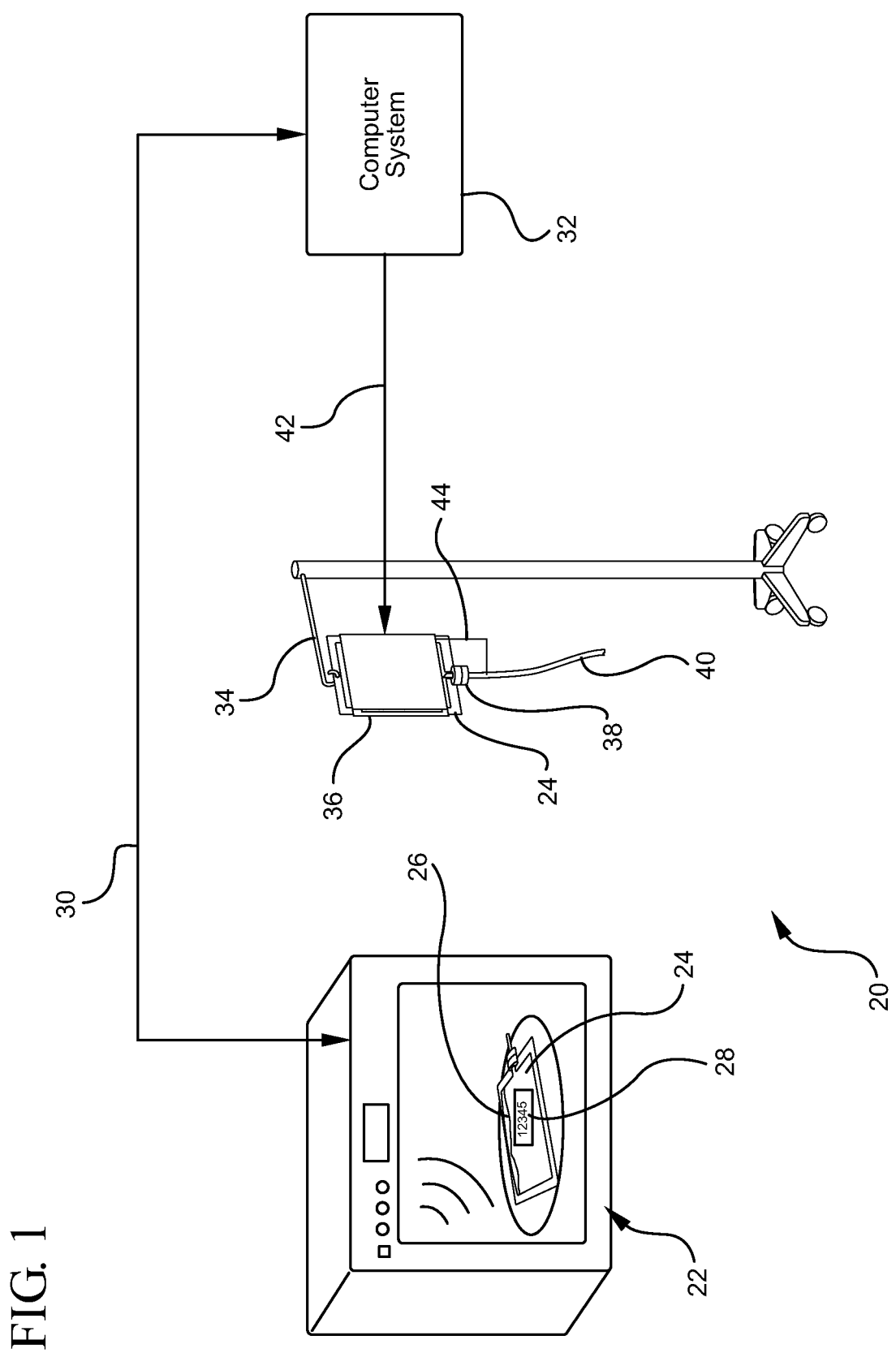
FIG. 1 is a perspective view of an embodiment of a system for heating and insulating contrast media in accordance with the present invention.

Referring now to FIG. 1, a system for heating and insulating contrast media is illustrated. The system generally comprises a preheating device 22, a container 24 containing contrast media fluid 26 (also referred to herein simply as "a container"), a thermal insulting cover 36, and an external computer system 32. The system facilitates the administration of preheated media contrast to a patient as well as automatically measuring and recording media contrast temperatures.

In some embodiments, the media contrast is preheated in a preheating device 22 prior to administration. One common heater 22 comprises an insulated body having an active heating element and a thermostat, which heats the media contrast to a predetermined temperature. Other various types of preheating devices can be used to heat the container of contrast media to the predetermined temperature. For example, in other embodiments, a heating or warming plate is used.

In some embodiments, it is advantageous to preheat the media contrast to a normal body temperature, approximately 98.6° so that it is comfortable to the patient when administered. Overly hot media contrast that is substantially hotter than a normal body temperature can cause trauma to the patient. However, in some embodiments, the media contrast is heated to a temperature that is greater than the natural body temperature of a patient in order to accommodate for the natural cooling of the contrast media prior to administration. Accordingly, in some embodiments, the preheating device preheats is capable and configured to preheat the media contrast to a predetermined temperature of approximately a normal body temperature. In other embodiments, the preheating device is configured to heat to a value within to a predetermined range. In some embodiments the range is within 1-4° Fahrenheit from the predetermined temperature. In some embodiments, the predetermined temperature is within 1-10° Fahrenheit of a normal body temperature.

As previously explained, some regulatory standards require that the temperature of heated medicaments be periodically checked and recorded. Accordingly, in some embodiments, the preheating device 22 is configured to record the temperature of the preheated contrast media. In some embodiments, the preheating device 22, automatically or manually identifies and/or records temperature data of the preheated container so that this information can be electronically recorded and transmitted to the computer system 32. A variety of devices and systems can measure temperature data, including electronic temperature sensors and thermometers. Additionally, a preheating device can be configured to and capable of heating the container of contrast media to the predetermined temperature. Alternatively, temperature data can be acquired via manual input, such as via a keypad in communication with or otherwise associated with the preheating device. In some embodiments, the preheating device 22 has predetermined heating schemes for heating a refrigerated container of media contrast 24 to the predetermined temperatures, based on prior heating experience. Accordingly, the preheating device 22 acquires the temperature of the program's intended final temperature as the temperature of the container of contrast media 24. Additionally, in some embodiments, the preheating device 22 includes a clock and the preheating device 22 records the time of the preheating process.

In some embodiments, the preheating device 22 reads the identification number or other identification data of the container that facilitates the association of the recorded temperature data with the specific container 24 of media contrast. Identification data can be associated with the temperature data, so that a record of which container was preheated and the preheated temperature can be made. In some embodiments, an identification element 28 includes the identification data of the container 24. For example, a container identification number, identification tag, a barcode, or an RFID tag can be included on the container 24. In some embodiments, the identification element 28 can be read electronically or automatically by the preheating device 22, such as with a barcode scanner, RFID reader, or the like. In other embodiments, the identification data is read via manual input, such as via a keypad in communication with or otherwise associated with the preheating device.

In some embodiments, after the container of media contrast is preheated, and after the preheated temperature and the identity of the container is recorded by the preheating device 22 the preheating device 22 transfers temperature and identification data to a computer system 32 via a communication link 30. In other embodiments, this data is transferred in real-time as it is acquired so that the preheating device 22 is not required to include storage circuitry. Accordingly, in some embodiments, the computer system 32 is an external computer system. In other embodiments, the computer system is an internal computer system within the preheating device 22.

In some embodiments, the computer system 32 prepares a compliant record based upon the received identification and temperature data. Accordingly, in some embodiments, the computer system includes record generating software or firmware which produces records of the preheating, heating, and periodic temperature readings of each container of contrast media 24, thus reducing the need to manually prepare such records.

In some embodiments, data is transferred between the preheating device 22 and the computer system via a data communicator (not shown) within or coupled to the preheating device 22. A data communicator comprises one or more electronic communication components configured to transmit data to an external computer system 32. In some embodiments, the data communication comprises a transmitter, a wireless transmitter, a modem, or other known communication components. In some embodiments the data communication comprises a communication link 30, which can be wireless or wired, direct or indirect. In some embodiments, this link includes a Bluetooth link. In some embodiments, the link comprises a connection port (not shown), such as a USB port, which can be accessed via a USB connector and information can be downloaded therethrough. In some embodiments, the preheating device 22 stores data relating to several container of media contrast, which is periodically transmitted to the computer system automatically or manually.

Various computer systems 32 can be incorporated into the system. For example, in some embodiments, the computer system 32 includes a network system of multiple interconnected computers. In some embodiments, the computer system 32 includes a single computer, such as a personal computer. Yet in other embodiments, the system includes a portable computing device, such as a PDA, smart phone, tablet computer, laptop, or equivalent structure.

With continued reference to FIG. 1, after the contrast media is preheated it can be used in imaging procedures. As illustrated in FIG. 1, it is common practice for the container of contrast media 24 to be coupled to tubing 40 and the container hung on an IV pole 34. The tubing allows the contrast media fluid to flow from the container 24 to an injector pump, to the patient, or to an imaging device. Tubing 40 is generally connected to the container 24 via a fluid spike 38, which pierces the container and creates a fluid channel through the spike and into the tubing 40.

Containers 24 for contrast media differ in size and structure. For example, some containers are capable of holding enough contrast media for multiple imaging procedures. Other containers hold only enough contrast media for a single imaging procedure. Furthermore, containers can be collapsible or rigid, large or small, and have thin or thick walls. Accordingly the components of the present system can be configured to accommodate these variations. When a large container of media contrast is used, there is generally a time gap between imaging procedures in which the contrast media may cool. Accordingly, in some embodiments, a thermal insulating cover 36 (also referred to herein simply as an "insulating cover") is provided to cover and insulate at least a portion of the container and assist the media contrast to retain its preheated temperature.

With continuing reference to FIG. 1, a thermal insulating cover 36 insulates the container 24. In some embodiments, the insulating cover 36 covers the entire container. In other embodiments, the insulating cover 36 covers only a portion of the container 24, such as a middle portion, a side portion, a bottom portion, a top portion, etc. Accordingly, the insulating cover 36 can have a variety of configurations, shapes, and sizes. In some embodiments, the insulating cover 36 is a sleeve that slips over or under the container 24. In some embodiments, the insulating cover 36 is wrap that wraps around a portion or the entire container 22. In some embodiments, the insulating cover 36 has approximately the same shape as the container 22, such that the insulating cover 36 entirely envelops the container. In some embodiments, the insulator includes a closed container. The insulating cover 36 can be made of a variety of insulators, for example, cloth, neoprene, rubber, vacuum space, Styrofoam, other known insulators, and combinations thereof. Examples of an insulating covers are illustrated in FIGS. 2-3B and described below.

In some embodiments, the insulating cover 36 comprises a heating element and a temperature sensor 38 for measuring the temperature of the contrast media fluid and heating the fluid if it begins to cool below an acceptable temperature level. Accordingly, in some embodiments, the combination of the temperature sensor and the heating element function as a thermostat that maintains the temperature of the media contrast within a predetermined temperature range or at a predetermined temperature. In some embodiments, the temperature sensor periodically measures the fluid temperature and a temperature controller adjusts the heating element periodically. Measurements can be taken at increments of 5 second, 10 seconds, 15 second, 20 seconds, 30 seconds, 45 seconds, 1 minute, 2 minutes, 3 minutes, 4 minutes, 5 minutes, 7 minutes, 10 minutes, 15 minutes, 20 minutes, 30 minutes, 45 minutes, 1 hour, or any period therebetween. Alternatively, the temperature sensor 37 can continuously take temperature measurements. Additionally, in some embodiments, the temperature controller records temperature measurements internally.

In some embodiments, the temperature sensor is disposed on the fluid spike 38 such that it is in direct contact with the contrast media. This configuration allows direct measurement of the fluid temperature at the location from which fluid is drawn or will be drawn from the container. The temperature sensor on the fluid spike can include a temperature probe, such as a thermo coupling, thermistor, or other like device on or near the tip of the spike. In some embodiments, the temperature sensor is in electronic communication via communication link 36 with components within the insulating cover 36, such as those described with reference to FIG. 2. In other embodiments, the temperature sensor is disposed outside of the container 24, and in contact with the outer surface of the container.

Figure 2:
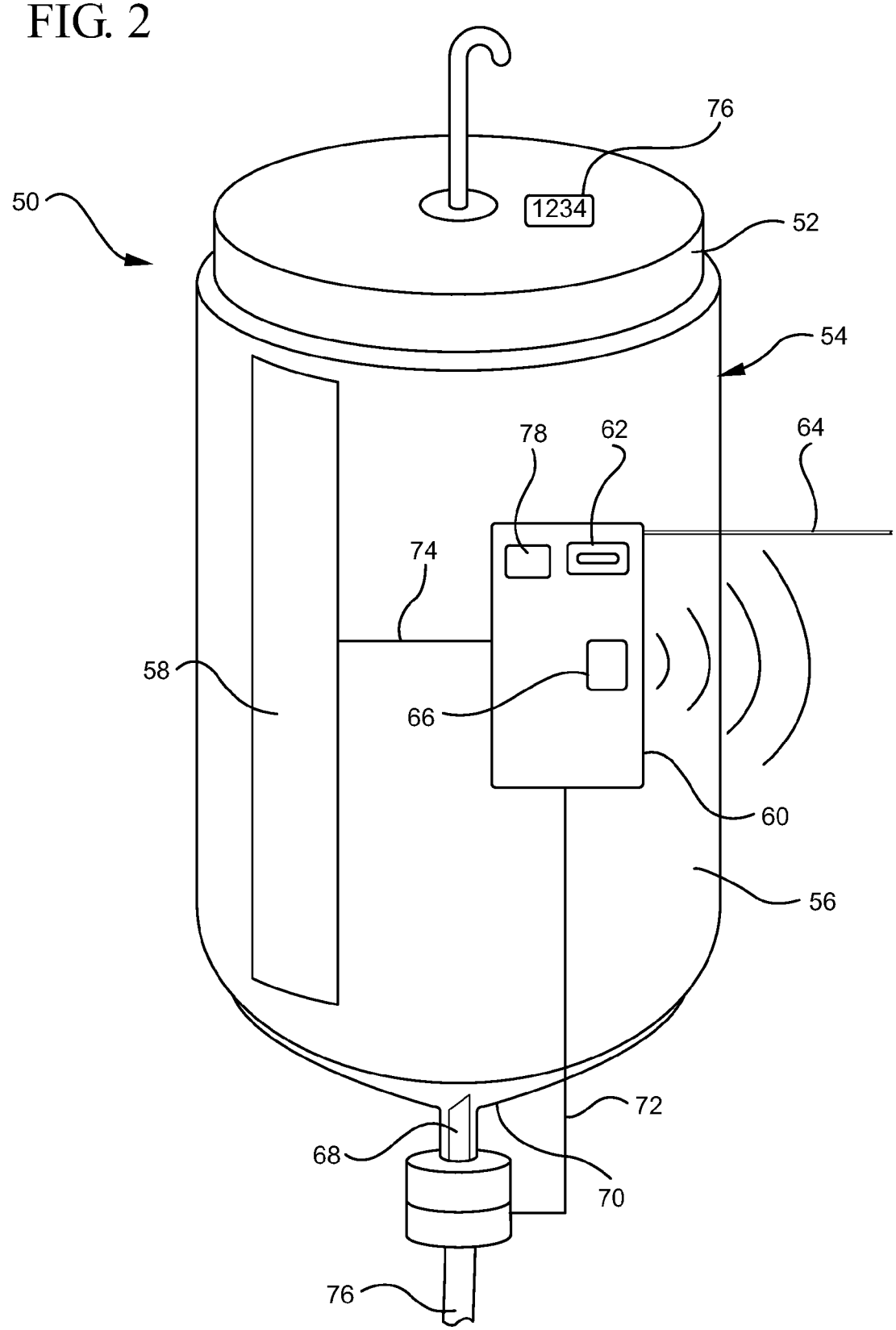
FIG. 2 is a perspective view of an embodiment of a container of contrast media having a thermal insulating cover in accordance with the present invention.

Referring now to FIG. 2, a container 52 of contrast media having a thermal insulating cover 50 is illustrated. The insulating cover 50 contains a heating element 58 that actively heats the container 52. In some embodiments, the heating element 58 is an ohmic heating element that heats as electricity flows through internal resistive material. In some embodiments, the insulating cover 50 includes a power supply, such as a battery, coupled to the temperature controller 60 for powering the temperature controller 60 and the heating element 58.

As illustrated, the insulating cover 50 contains a temperature controller 60, which is in electronic communication with the heating element 58 and controls the heating element 58. The temperature controller 60 is also in electronic communication with the temperature sensor 70. In this configuration, the temperature controller 60 is configured to function as a thermostat, to regulate the temperature of the container of contrast media 52 in order to maintain it within a predetermined temperature range or at a predetermined temperature. Accordingly, in some embodiments, the temperature controller has logical controls that respond to temperature data received from the temperature sensor by turning on or off the heating element 58. Thus, the temperature controller 60 can maintain the temperature of the media contrast within a predetermined range or at a predetermined value. In some embodiments, the temperature controller 60 is in wireless electronic communication with the temperature sensor 70. In other embodiments, the link 72 is wired. In some embodiments, the temperature sensor is integral with the temperature controller 60.

Similar to the preheating device 22 of FIG. 1, in some embodiments, the temperature controller 60 reads the identification number or other identification data from an identification element 76 on the container. For example, in some embodiments, the temperature controller 60 includes an RFID reader 78 or other identification reader for reading temperature data from an RFID identification element 76 on the container 52. Again, similar to the preheating device 22, in some embodiments, the temperature controller 60 transfers temperature and identification data to a computer system 32 via a communication link and using a data communicator. In some embodiments, data is transferred in real-time as it is acquired so that the temperature controller 60 is not required to include storage circuitry. In other embodiments, the temperature controller 60 includes a storage device for storing temperature and identification data. Accordingly, in some embodiments, the computer system 32 is an external computer system. In other embodiments, the computer system 32 is internal to the temperature controller 60 or the insulating cover 50.

From the foregoing it will be seen that the system includes a temperature controller 60 that automatically maintains the temperature of the contrast media fluid at a predetermined temperature or within a predetermined temperature range. Additionally, a data communicator is configured to transmit temperature readings and container identification to an external computer 32. In some embodiments, these processes take place automatically or semi-automatically, such that they dramatically decrease the manual work required by medical personnel.

In some embodiments, the insulating cover 50 comprises additional system features and/or components with additional benefits and functionality. For example, in some embodiments, the system comprises a storage device (not shown) for storing temperature data, time data, and/or identification data before this data is transferred to the computer system 32. In some embodiments, the temperature controller 60 comprises an internal clock for recording the time when measurements are taken. In some embodiments, a display, such as an LCD display (not shown), is coupled to the insulating cover 50 for displaying data, such as the temperature of the container 52. In some embodiments, the system comprises an input device, such as a keypad, touchpad, or the like for manually inputting identification data or other data. The input device may be coupled to the temperature controller 60 or to the data communicator. In some embodiments, the temperature controller 60 comprises a data communicator integral with the temperature controller 60 for transmitting data from the controller to an external computer system 32. In some embodiments, the temperature controller 60 or the data communicator comprises a transmitter 66, a port 62, and/or a wired link 64 for communicating with external computer systems 32 for transmitting data to a computer system. In some embodiments, the temperature controller 60 comprises a port or connector (not shown) that connects to a separate input device to receives data therefrom. Examples of separate input devices include keyboards, barcode readers, RFID reader, and measurement sensors. Thus, in some embodiments, the temperature controller 60 controls more than the temperature of the container, but controls a recording and transmission system as well.

Depending on the functions of the temperature controller 60, it may include a variety of component configurations. In some embodiments, the temperature controller 60 includes a processor, a storage device, a communication driver, and a communication port. In some embodiments, the temperature controller 60 includes a processor having firmware and/or software. In some embodiments, the temperature controller 60 includes multiple processors, each processor designated for specific purpose, such a temperature control, identification reading, identification data transmission, or correlation of temperature and time data. In some embodiments, the temperature controller 60 is housed within or otherwise coupled to the insulating cover 50. In some embodiments, the temperature controller 60 includes combinations of the aforementioned components. In some embodiments, the temperature controller 60 is located on the container 52, on the hanger 34, on the insulating cover 50, or in a nearby location.

Figure 3A:
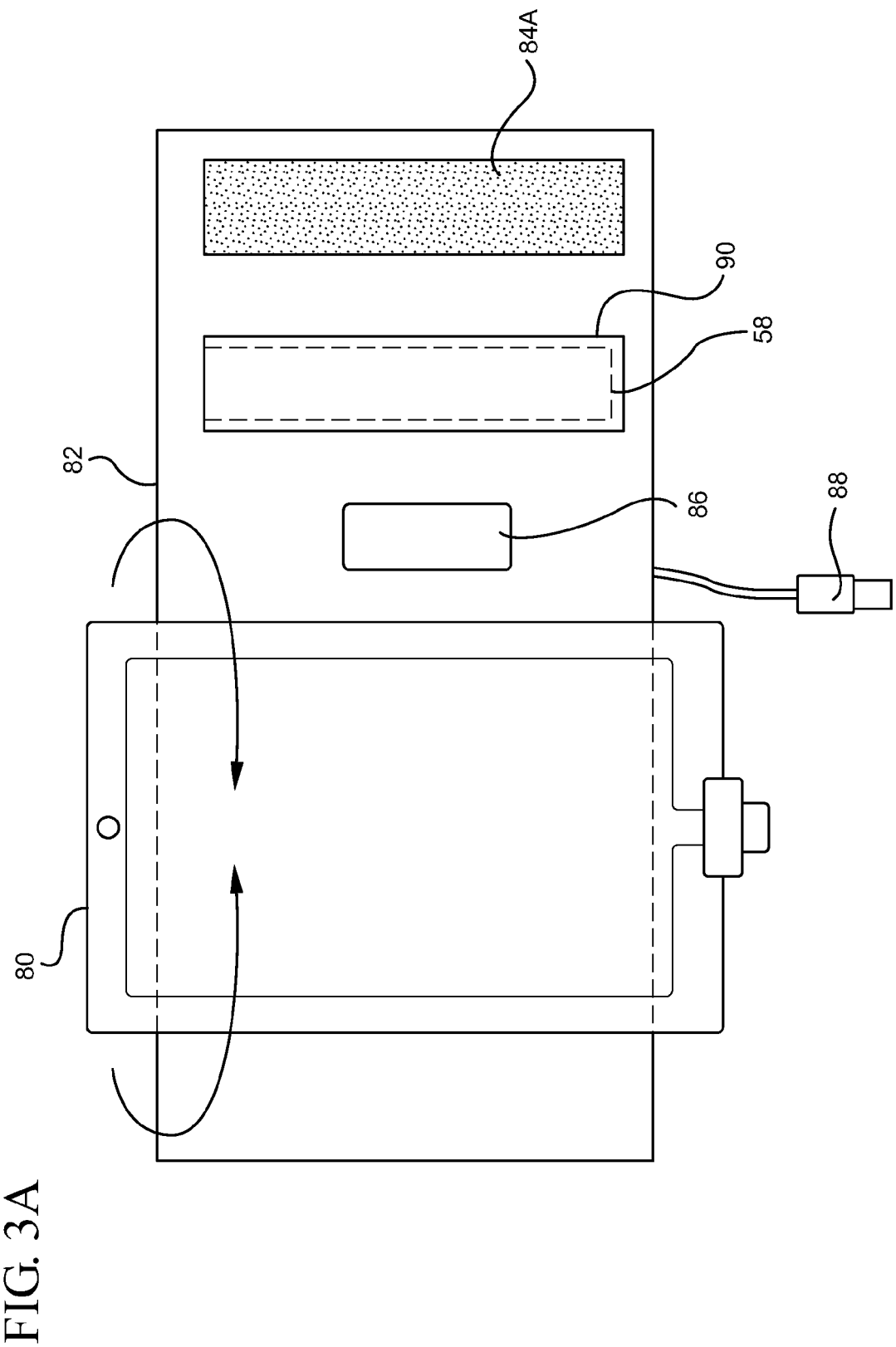
FIG. 3A is a perspective view of an embodiment of a thermal insulating cover in accordance with the present invention.
Figure 3B:
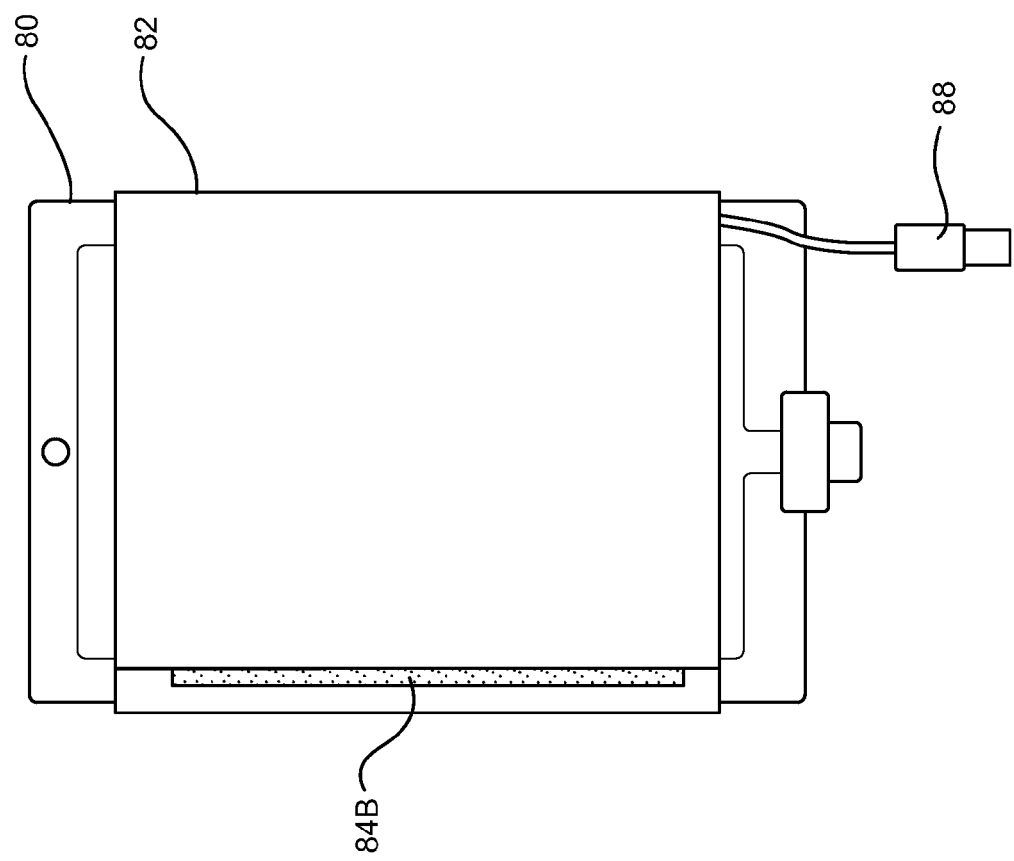
FIG. 3B is another perspective view of the embodiment of a thermal insulating cover of FIG. 3A.

Referring now to FIGS. 3A and 3B, a thermal insulating cover 82 in the form of a wrap is illustrated. To accommodate for a variety of container sizes, in some embodiments, the insulating cover 82 is adjustable. Accordingly, the insulating wrap 82 has a connector 84a, such as a Velcro strip, which connects to a second connector 84b on the insulating wrap 82 and can be adjusted to fit around various sizes of containers 80. Additionally, in some embodiments, an insulting wrap 82 includes a strap (not shown) that extends from one side of the cover, over the top of the container, and connects to the other side of the cover.

FIG. 3A illustrates an insulating cover 82 having a pocket 90 for receiving a removable heating element 58. When a preheated container of media contrast 80 is covered in the insulating cover 82, only a small amount of energy may be required to maintain the container at a predefined, preheated temperature. Accordingly, in some embodiments, a powered electronic heating element is replaced by inserting an independent heating element into the sleeve 58 and wrapping the sleeve around the container 80. One example of an independent heating element comprises an air-activate chemical warmer. Because an independent heating element is not controlled by a temperature controller, in some embodiments, no temperature controller is used. Accordingly, in some embodiments, the temperature sensor 86 includes a storage device for recording periodical temperature measurements. In other embodiments, the temperature sensor 86 directly transmits temperature data to an external computer system 32. The temperature sensor 86 can thus be accessed via a port 88.

From the foregoing it will be seen that the present system and the embodiments described herein can implemented a method for heating and insulating contrast media. In some embodiments, a container containing contrast media fluid is preheated. Before, during or after preheating, the container's identification number is read or otherwise identified and the temperature of the preheated container is identified. This information is then communicated to a computer system.

In some embodiments, the method also includes covering at least a portion of a container of the contrast media in a thermal insulating cover. In some embodiments the container is preheated, while in other embodiments, the container is not preheated. While covered by the thermal insulating cover, the temperature of the contrast media or the container is periodically measured. Next, the measured temperature is communicating to a temperature controller, which determines if the measured temperature is below a threshold temperature. If the measured temperature is below a threshold temperature then the contrast media is heated. Accordingly, if the container is not preheated, the heater of the insulating sleeve can both preheat to and maintain the container at a predetermined temperature. At some time after measuring the temperature, a data communicator transfers the measured to a computer system. Additionally, in some embodiments, the container's identification number is read or otherwise identified and then communicated to a computer system. Lastly, in some embodiments, the computer system prepares a record of the measured temperatures and the times of the measurements.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A system for heating and insulating contrast media and for facilitating the generation of reports regarding the heating of contrast media, the system comprising:
    a thermal insulating wrap sized to cover at least a portion of a contrast media container containing contrast media fluid when wrapped around the contrast media container, the thermal insulating wrap comprising:
        a heating element coupled to the thermal insulating wrap;
        a temperature sensor, coupled to the thermal insulating wrap, the temperature sensor being configured to be in contact with at least one of a contrast media container and contrast media fluid contained within the contrast media container when the contrast media container is contained within the thermal insulating wrap;
        a temperature controller, coupled to the thermal insulating wrap, in electronic communication with the heating element and the temperature sensor, the temperature controller having logical controls that receive contrast media temperature data from the temperature sensor and control the function of the heating element, the temperature controller further including an identification reader for identifying a unique identifier contained on a contrast media container while the contrast media container is contained within the thermal insulating cover such that multiple contrast media containers can be uniquely identified by the identification reader when any of the multiple contrast media containers are contained within the thermal insulating wrap thereby facilitating the identification of which contrast media container is contained within the thermal insulating wrap at a particular time; and
        a data communicator, coupled to the thermal insulating wrap, configured to receive temperature data and a unique identifier of a contrast media container while the contrast media container is contained within the thermal insulating wrap, the data communicator being further configured to transmit the temperature data and the unique identifier of the contrast media container to an external computer system while the contrast media container is contained within the thermal insulating wrap to thereby enable the external computer system to maintain a record of the temperature of contrast media within any contrast media container that is uniquely identified by the identification reader of the thermal insulating wrap.

2. The system of claim 1, further comprising a preheating device.

3. The system of claim 2, wherein the preheating device includes a data communicator to transmit contrast media temperature data to an external, electronic database.

4. The system of claim 1, wherein identifying a unique identifier contained on a contrast media container comprises reading an element attached to the contrast media container.

5. The system of claim 4, wherein the element attached to the contrast media container is an RFID tag.

6. The system of claim 1, wherein the temperature data includes periodic temperature measurements of the contrast media fluid temperature.

7. A thermal insulating wrap for a contrast media container, the thermal insulating wrap comprising:
    a heating element for heating contrast media of a contrast media container contained within the thermal insulating wrap;

a temperature sensor for sensing the temperature of the contrast media while the contrast media container is contained within the thermal insulating wrap;

a temperature controller in electronic communication with the heating element and the temperature sensor, the temperature controller having logical controls that receive contrast media temperature data from the temperature sensor and control the function of the heating element;

an identification reader for reading an identification element attached to the contrast media container contained within the thermal insulating wrap to obtain a unique identifier of the contrast media container such that multiple contrast media containers can be uniquely identified by the identification reader when any of the multiple contrast media containers are contained within the thermal insulating wrap thereby facilitating the identification of which contrast media container is contained within the thermal insulating wrap at a particular time; and a data communicator configured to receive the temperature data and the unique identifier of the contrast media container while the contrast media container is contained within the thermal insulating wrap, the data communicator being further configured to transmit the temperature data and the unique identifier of the contrast media container to an external computer system while the contrast media container is contained within the thermal insulating wrap to thereby enable the external computer system to maintain a record of the temperature of the contrast media within the contrast media container, the record being associated with the contrast media container having the unique identifier transmitted with the temperature data.

8. The thermal insulating wrap of claim 7, wherein the data communicator transmits the temperature data and the unique identifier using a wireless protocol.

9. The thermal insulating wrap of claim 7, wherein the temperature sensor is disposed on a fluid spike.

10. The thermal insulating wrap of claim 7, wherein the heating element is an active heating element.

11. The thermal insulating wrap of claim 7, wherein the heating element is an ohmic heating element.

12. A thermal insulating wrap for heating and insulating a contrast media container and for transmitting temperature and identification data to a separate computing system, the thermal insulating wrap comprising:

flexible insulating material having a shape for covering a portion of a contrast media container when the thermal insulating wrap is wrapped around the contrast media container;

one or more heating elements attached to the flexible insulating material;

one or more temperature sensors for detecting a temperature of contrast media within a contrast media container contained within the flexible insulating material;

a temperature controller that receives temperature readings from the one or more temperature sensors and controls the one or more heating elements based on the temperature readings;

an identification reader attached to the flexible insulating material that detects a unique identifier of a contrast media container by reading an element attached to the contrast media container; and a data communicator, attached to the flexible insulating material, that receives temperature readings from the temperature controller and a unique identifier from the identification reader while a contrast media container is contained within the flexible insulating material, the data communicator further periodically transmitting the temperature readings and the unique identifier of the contrast media container to a separate computing system to enable the separate computing system to create a record of the temperature readings of a specific contrast media container as identified by the unique identifier received with the temperature readings.

13. The thermal insulating wrap of claim 12, wherein the data communicator transmits temperature readings and unique identifiers to the separate computing system using a wireless protocol.

14. The thermal insulating wrap of claim 12, wherein the identification reader is an RFID reader that reads an RFID tag contained on a contrast media container contained within the flexible insulating material.

* * * * *